(12) United States Patent
Pedrazzini

(10) Patent No.: US 9,989,545 B2
(45) Date of Patent: Jun. 5, 2018

(54) APPARATUS FOR THE STORAGE AND RETRIEVAL OF LARGE VOLUMES OF TEST TUBES

(71) Applicant: INPECO HOLDING LTD., Qormi, QRM (MT)

(72) Inventor: Gianandrea Pedrazzini, Paradiso (CH)

(73) Assignee: INPECO HOLDING LTD., Qormi, QRM (MT)

(*) Notice: Subject to any disclaimer, the term of this patent is extended or adjusted under 35 U.S.C. 154(b) by 16 days.

(21) Appl. No.: 15/313,590

(22) PCT Filed: May 27, 2015

(86) PCT No.: PCT/EP2015/061643
§ 371 (c)(1),
(2) Date: Nov. 23, 2016

(87) PCT Pub. No.: WO2015/181202
PCT Pub. Date: Dec. 3, 2015

(65) Prior Publication Data
US 2017/0219616 A1    Aug. 3, 2017

(30) Foreign Application Priority Data

May 28, 2014  (IT) .............................. MI2014A0984

(51) Int. Cl.
*G01N 1/00* (2006.01)
*G01N 35/00* (2006.01)
*G01N 35/04* (2006.01)
(52) U.S. Cl.
CPC ......... *G01N 35/0099* (2013.01); *G01N 35/04* (2013.01); *G01N 2035/041* (2013.01); *G01N 2035/0425* (2013.01); *G01N 2035/0462* (2013.01); *G01N 2035/0465* (2013.01)

(58) Field of Classification Search
CPC .......................... G01N 35/00; G01N 35/0099
USPC .................................................... 422/50, 500
See application file for complete search history.

(56) References Cited

U.S. PATENT DOCUMENTS

| 5,233,844 A | 8/1993 | Knippscheer et al. |
| 2004/0037679 A1 | 2/2004 | Sato et al. |
| 2005/0075757 A1 | 4/2005 | Haas et al. |
| 2008/0213080 A1 | 9/2008 | Cachelin et al. |
| 2011/0045958 A1 | 2/2011 | Pedrazzini |
| 2013/0017535 A1 | 1/2013 | Frey et al. |
| 2013/0085597 A1 | 4/2013 | Koch et al. |
| 2013/0116102 A1 | 5/2013 | Hansen |

FOREIGN PATENT DOCUMENTS

WO    2014/071214 A1    5/2014

OTHER PUBLICATIONS

International Search Report, dated Sep. 2, 2015 (3 pages).

*Primary Examiner* — Jyoti Nagpaul
(74) *Attorney, Agent, or Firm* — Jacobson Holman, PLLC.

(57) ABSTRACT

There is described an apparatus for depositing and retrieving large volumes of test tubes in/from a warehouse, comprising an input/output module of a first and a second container with a plurality of test tubes, a multiple pick up device of test tubes, a single pick up device of test tubes, a first and second station for the provisional allocation of said containers and a motorized traveling lift able to carry said first and second container simultaneously on two distinct coplanar locations.

8 Claims, 22 Drawing Sheets

APPARATUS FOR THE STORAGE AND RETRIEVAL OF LARGE VOLUMES OF TEST TUBES

BACKGROUND OF THE INVENTION

The present invention relates to an apparatus for the storage and retrieval of large volumes of test tubes.

Nowadays, in the context of laboratory automation systems used for handling test tubes containing samples of biological material, the need is increasingly felt to have suitably refrigerated warehouses within the system itself in which the analyzed biological samples can be stored for a more or less long period, so as to make them available to the system again, when needed, to repeat the analysis by the modules connected to the automation.

Patent application MI2012A002011 by the same Applicant describes an apparatus for automatically depositing, storing and retrieving samples of biological material in/from a refrigerated warehouse using two distinct static robots.

Disadvantageously, the apparatus described in said patent application is not suitable for large-sized warehouses.

On the other hand, given the ever-increasing operating volumes of a laboratory, it is desirable that the storage and subsequent retrieval involves as many samples as possible.

BRIEF SUMMARY OF THE INVENTION

The object of the present invention is to provide an apparatus for the storage and retrieval of large volumes of test tubes in/from large-sized warehouses ensuring the same throughput as the storage solutions already known.

A further object of the present invention is that said apparatus can carry out a selective retrieval of samples, even if positioned in different and very far areas of the warehouse.

Moreover, since the test tubes inserted in the warehouse may require, depending on the type of biological sample they contain, different storage times, yet a further object of the present invention is that said apparatus is capable of storing substantially at the same time all the test tubes containing samples of the same type, so as to have a certain uniformity in the processing times of the same and thus be able to retrieve them easily when their storage time comes to an end; in other words, in the event that the life time of the samples ends without the need to direct them again along the automation for new analysis, these must be disposed of all together in the most practical possible manner.

These and other objects are achieved by an apparatus for the storage and retrieval of large volumes of test tubes in/from a warehouse, characterized in that it comprises an input/output module of test tubes from/to an automation system for the transport of said test tubes in transport devices of single test tubes, which includes two distinct coplanar locations for a first and a second container of a plurality of test tubes, a multiple pick up device adapted to pick up said test tubes from a plurality of transport devices of single test tubes queued in a secondary lane of said automation system, and to release them in the first container positioned on an input/output module, a single pick up device adapted to pick up said test tubes from the second container positioned on said input/output module and to release them in said transport devices of single test tubes on said automation system, a first station for the provisional allocation of said containers on distinct locations of a same shelf comprising one or more shelves and interfaced with said input/output module, a second station of the provisional allocation of the first container on one or more shelves, interfaced with a discharge device of test tubes to be disposed, a motorized traveling lift able to simultaneously transport on two distinct coplanar locations said first and second container, and adapted to move bidirectionally said first and second container of test tubes between said first station for the provisional allocation and said warehouse, and only said first container between said warehouse and said second station for the provisional allocation.

BRIEF DESCRIPTION OF THE DRAWINGS

These and other features of the present invention will appear more clearly from the following detailed description of an embodiment thereof, shown by way of a non-limiting example in the accompanying drawings, in which.

DETAILED DESCRIPTION OF THE INVENTION

Figure 1:
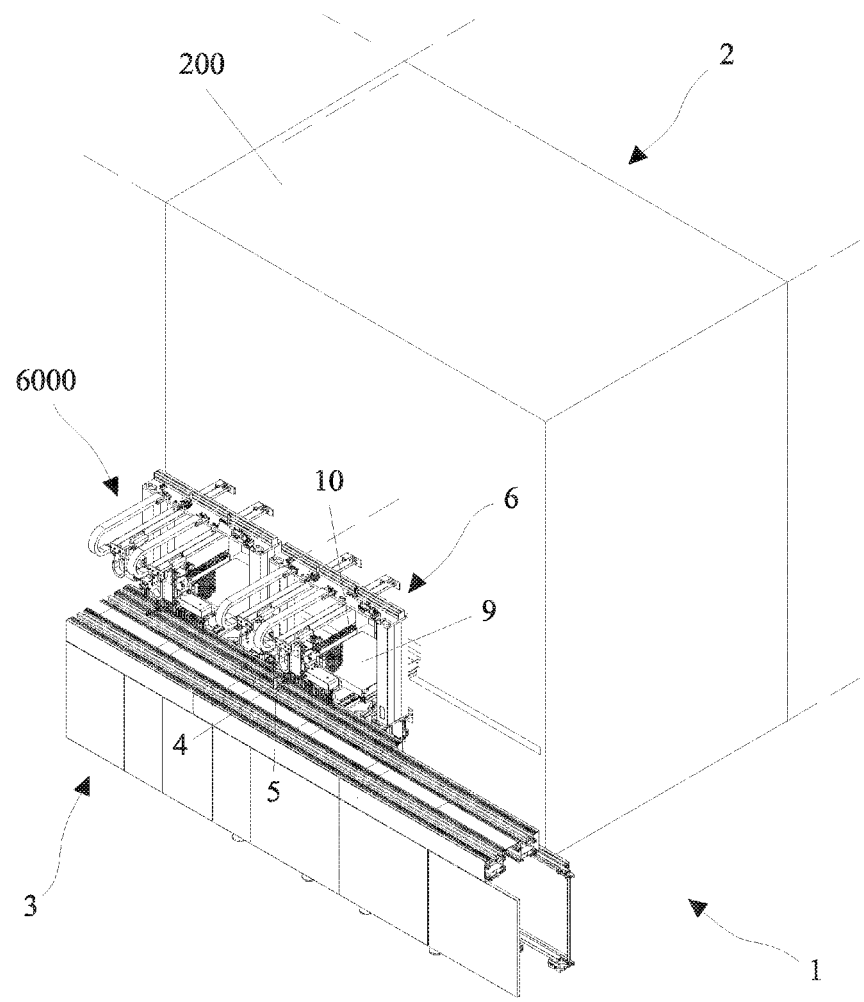
FIG. 1 shows a perspective view of an input/output module of samples and of a warehouse.

An apparatus 1 for the automatic deposit, storage and retrieval of samples of biological material in/from a refrigerated warehouse 2, whose temperature typically ranges from −2 to +6° C., is shown in FIG. 1.

Warehouse 2 is facing a laboratory automation system 3 which carries samples of biological material contained in test tubes 4 inserted in turn into transport devices 5. The interfacing between warehouse 2 and system 3, with relative exchange of test tubes 4, is implemented by means of a sample input/output module 6.

Figure 2:
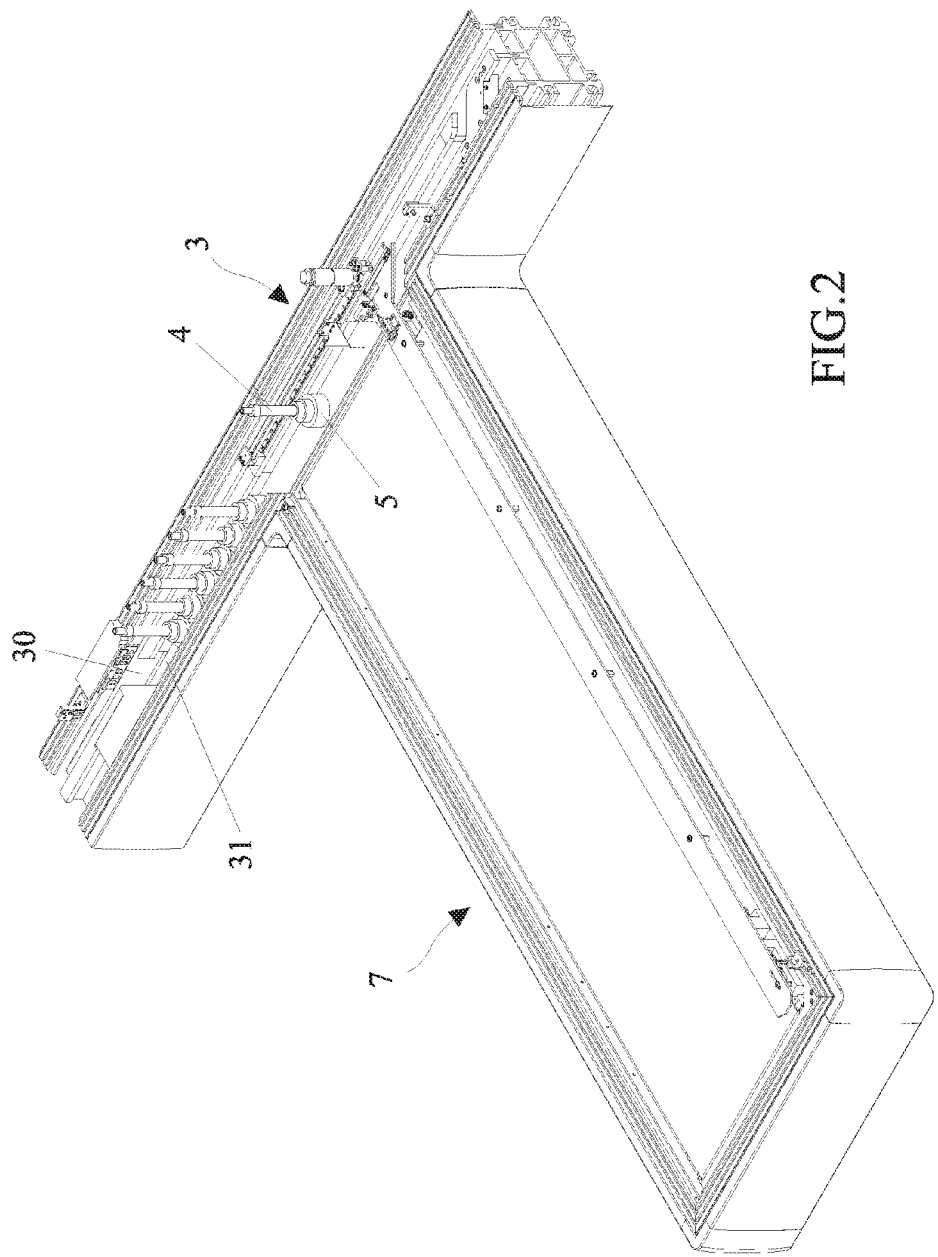
FIG. 2 shows a perspective view of a station for the provisional allocation of biological samples.

Moreover, along the automation system 3 and upstream of the interface with warehouse 2, one or more stations 7 may be provided for the provisional allocation of biological samples, i.e. test tubes 4 contained in the relative transport devices 5 of single test tubes 4, similar to those described in Italian patent application MI2012A 001218 (FIG. 2). The presence of more than one of such stations 7 can serve to park, in each of them, generally homogeneous samples in terms of storage time which they subsequently need inside warehouse 2.

Figure 3:
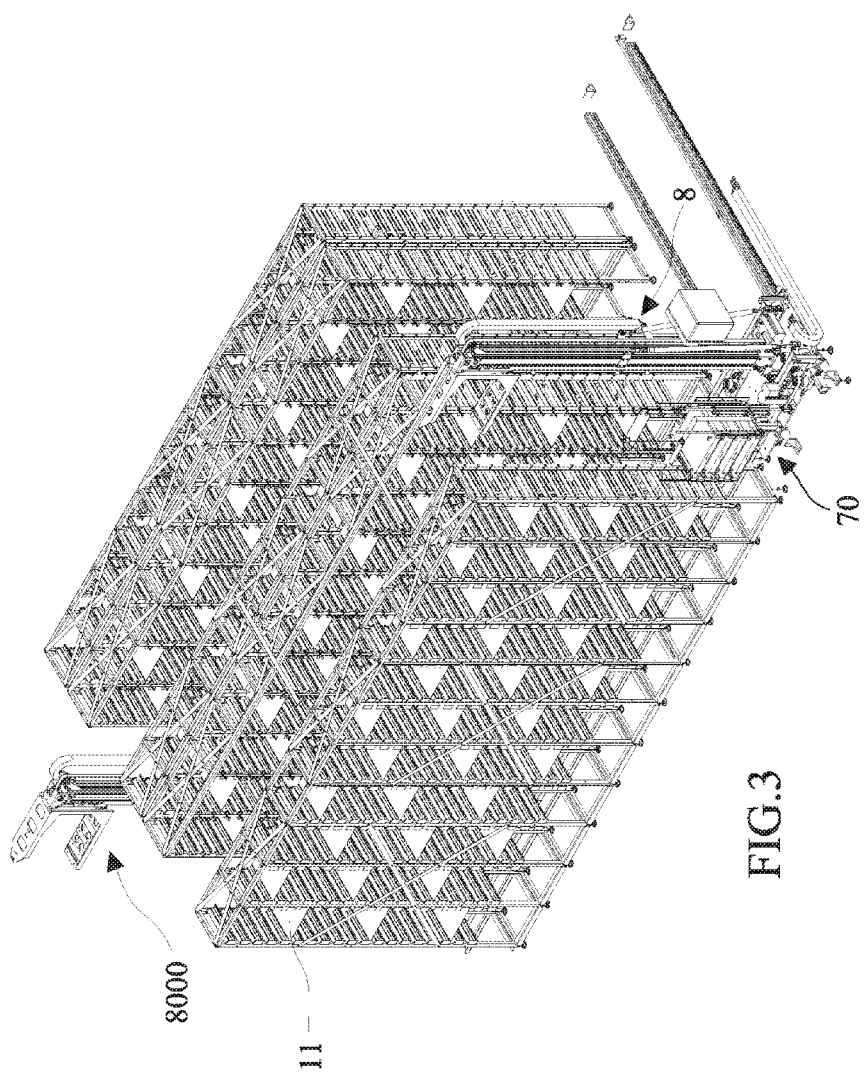
FIG. 3 shows a perspective view of a traveling lift and of the interior of the warehouse.
Figure 4:
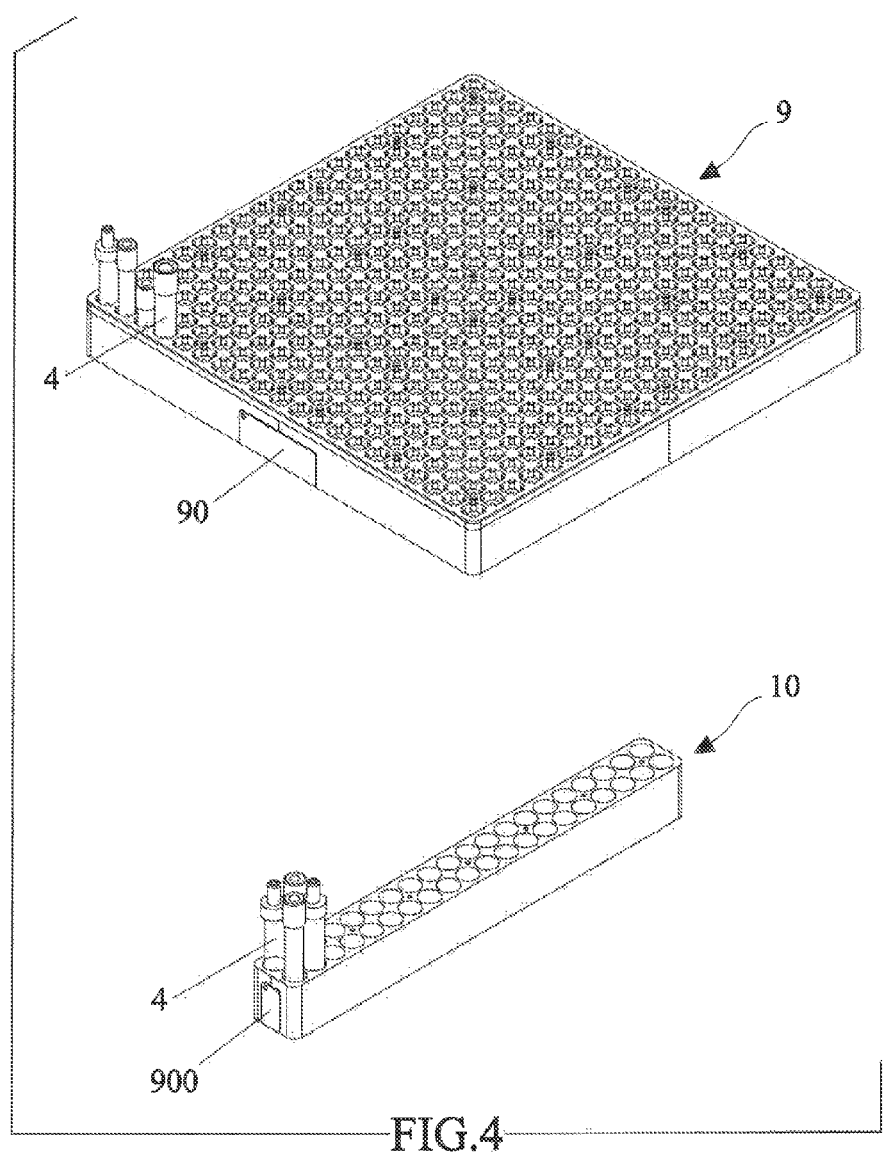
FIG. 4 shows in detail the containers of test tubes used.

A motorized traveling lift 8 (FIG. 3) moves along rails inside warehouse 2, able to carry on board simultaneously both a container 9 ("rack") for the test tubes 4 to be deposited in warehouse 2 and a container 10 for the test tubes to be retrieved from the inside of magazine 2 for their subsequent reintroduction along the automation system 3 (FIG. 4).

The traveling lift 8, moving along appropriate rails inside warehouse 2 itself, is able to position itself in front of any of locations 11 of warehouse 2 adapted to accommodate a container 9, and at this point two opposite operations may be carried out: a container 9 may be removed from location 11 and positioned on the traveling lift 8, so that one or more test tubes 4 are picked up from it, or conversely if the traveling lift 8 is already carrying a container 9 (filled with test tubes 4 just unloaded from the automation system 3), it is moved to location 11 for medium/long term storage.

Figure 5:
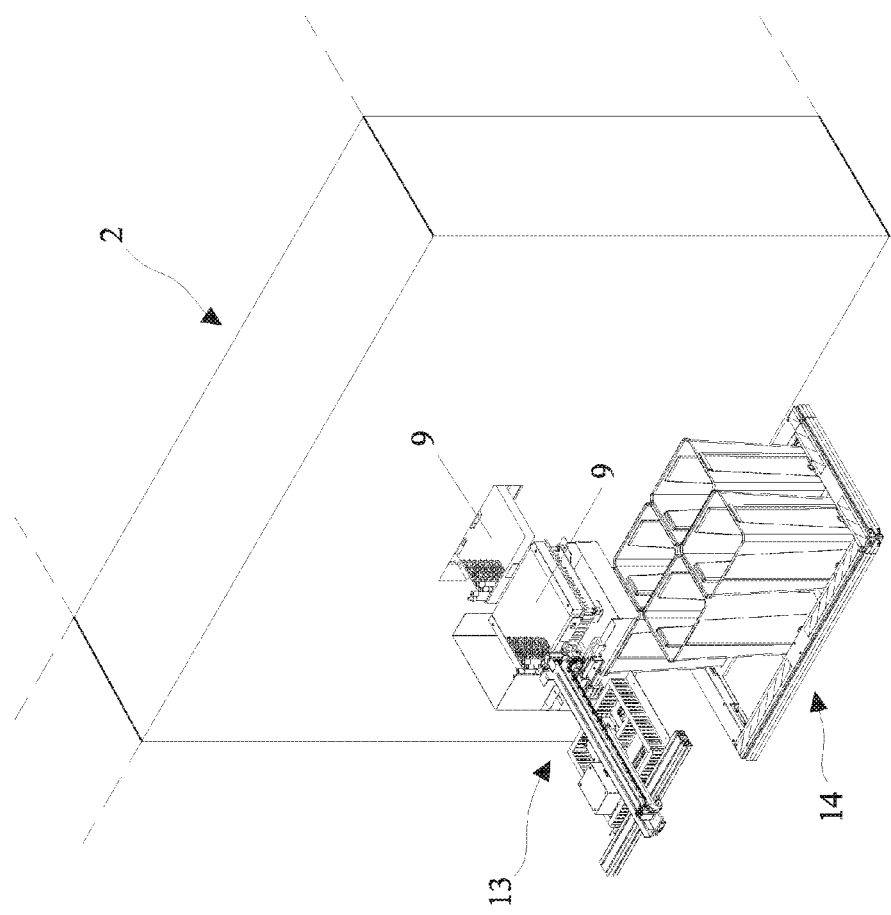
FIG. 5 shows a perspective view of the warehouse, of a test tube discharge device and of an apparatus with multiple racks for the collection of test tubes.

Along the face of warehouse 2 opposite the one which interfaces with the automation system 3 is a discharge device 13 of the test tubes 4 which have reached the end of their life cycle and which therefore, containing samples that cannot be meaningful anymore for new analysis, must be disposed of (FIG. 5).

To this end, an apparatus with multiple racks 14 may be provided underneath such a discharge device for collecting the disposed test tubes 4, similar to that described by Italian patent application MI2012A 001111 (FIG. 5).

Figure 6:
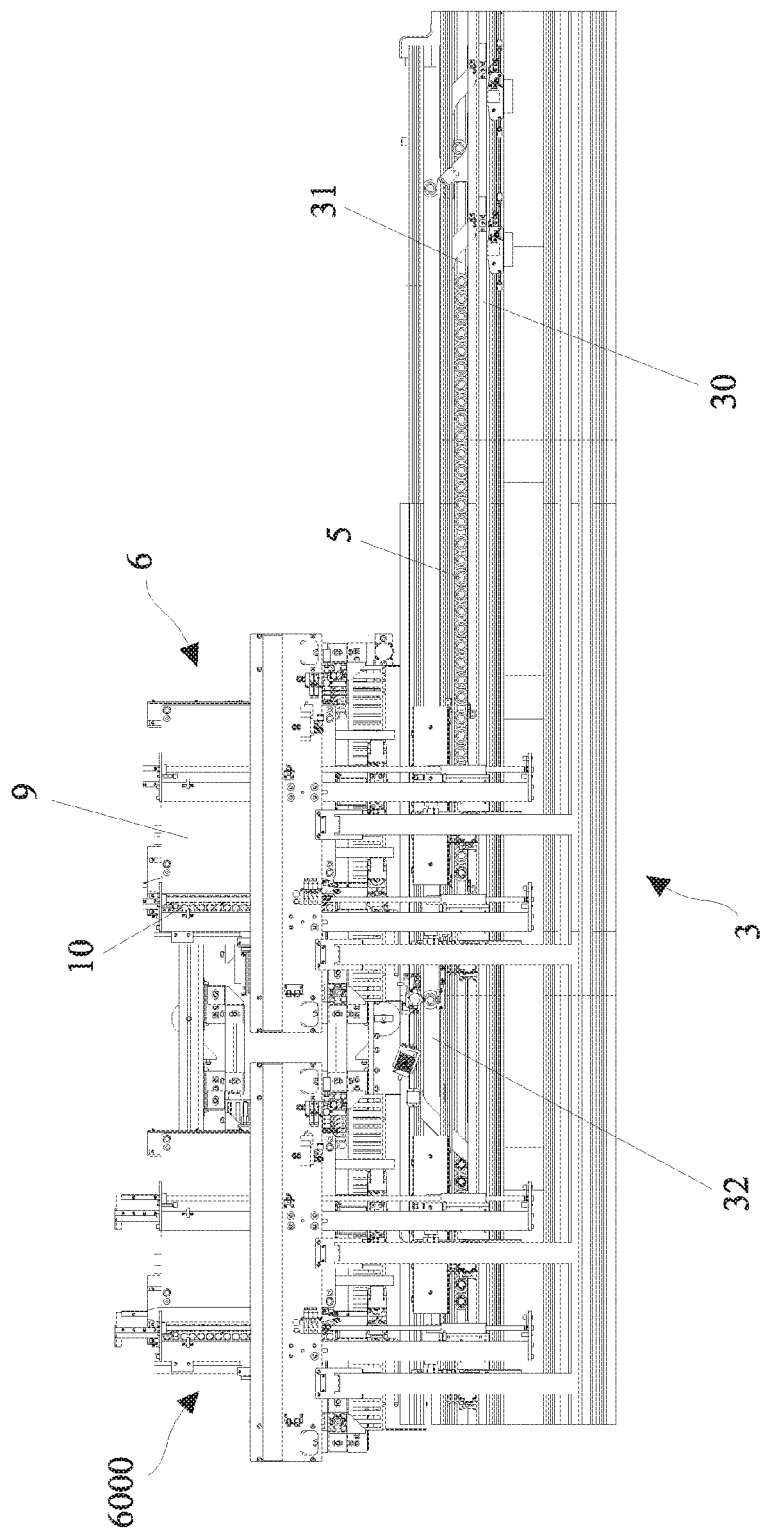
FIG. 6 shows a top plan view of the automation system and of the sample input/output module.

Describing in more detail the operation of apparatus 1, the test tubes 4 traveling along the automation system 3 and which must be allocated in warehouse 2 are suitably diverted from a main lane 30 to a secondary lane 31 of system 3, so as to form a queue of transport devices 5 with single test tube 4 in the sampling point of the input/output module 6 (FIG. 6).

The transport devices 5 with test tube 4, before interfacing with the input/output module 6, as mentioned, may also be diverted even more upstream in one or more stations 7 for the provisional allocation of biological samples. Each of said stations 7 is designed to allocate test tubes 4, preferably containing samples homogeneous by type, and which therefore once released and directed to the interface with the input/output module 6 typically require similar storage times inside warehouse 2 (FIG. 2).

Figure 7:
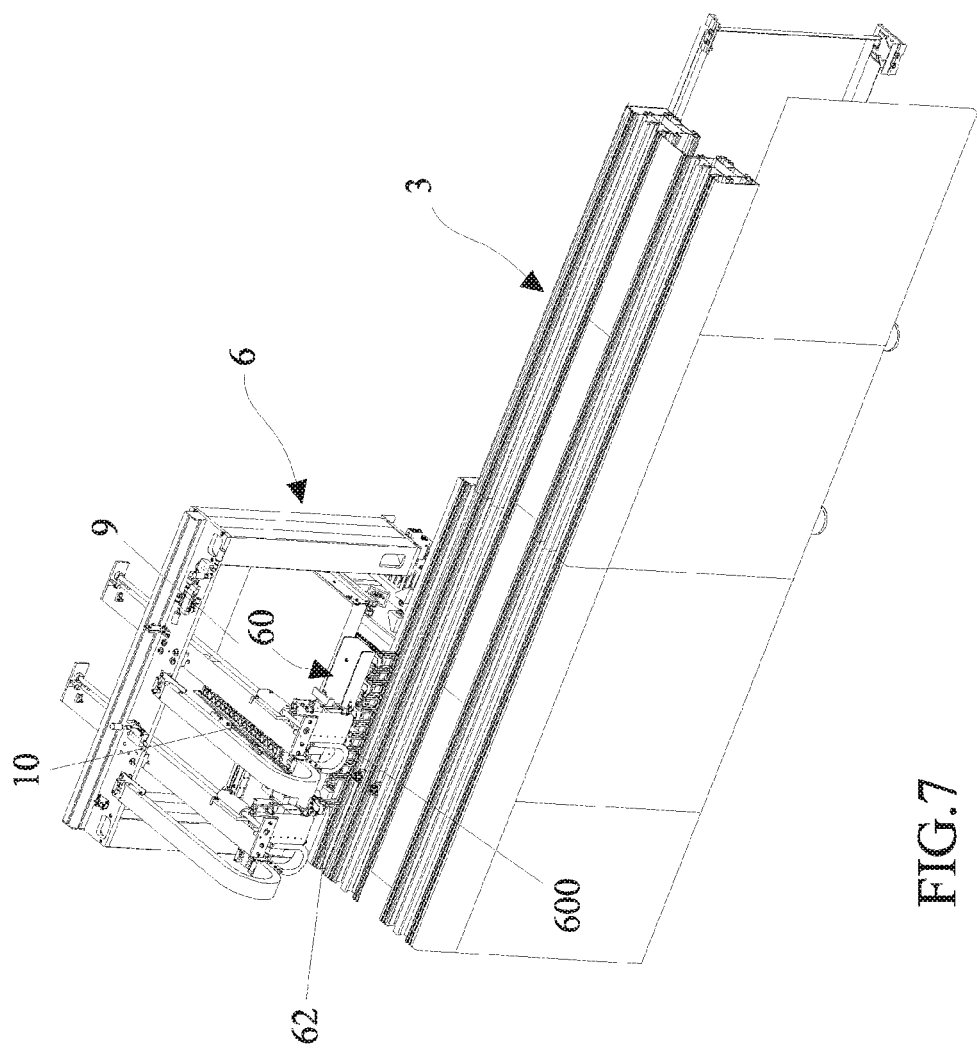
FIG. 7 shows a top perspective view of the automation system and of the sample input/output module.
Figure 8:
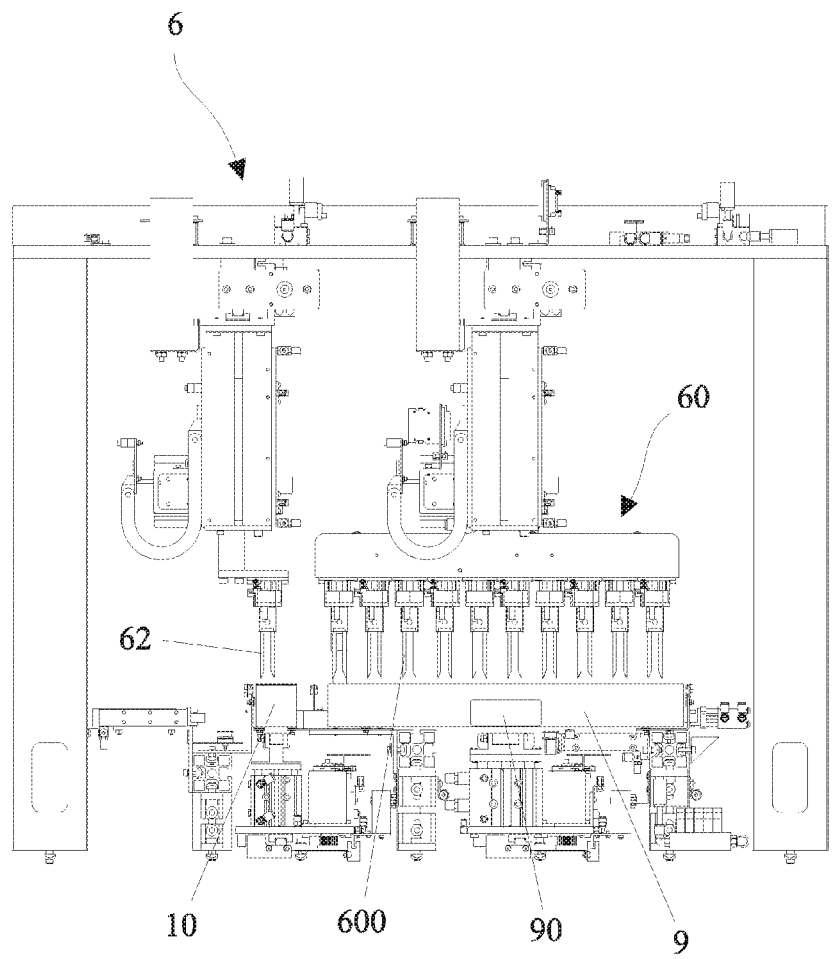
FIG. 8 shows a front view of the sample input/output module.

The test tubes 4 contained in the queued transport devices 5 are at this point picked up by a multiple pick up device 60 wherein the distance between each of the single pick up devices 600 is suitably calibrated on the distance between the test tubes 4 of two adjacent transport devices 5 in the queue (FIG. 7-FIG. 8). The multiple pick up device 60, moving along the Cartesian axes, is positioned above the empty container 9 waiting on the input/output module 6 and unloads the test tubes 4 in their locations.

Figure 9:
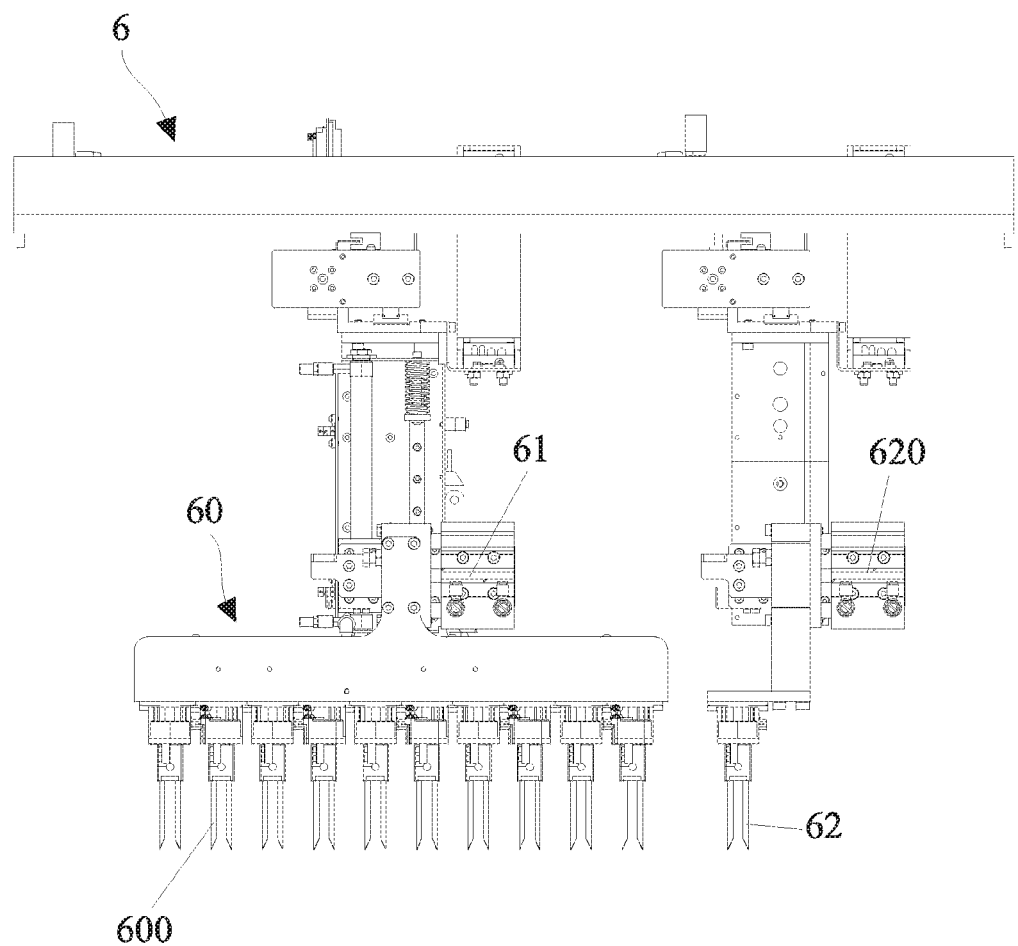
FIG. 9 shows an enlarged rear view of the sample input/output module in FIG. 8, with in detail the single and multiple pick up devices.

Meanwhile, the queue of transport devices 5 advances and the pick up device 60 returns to the interface with the secondary lane 31 of system 3, to pick up new test tubes 4 which are then inserted into container 9, in the remaining locations on the same row. This is made possible by the fact that, along the direction parallel to system 3, the pick up device 60 is able to perform a further movement, controlled by a pneumatic cylinder 61 and of width equal to half the pitch between two pick up fingers (FIG. 9); in this way, two successive sets of test tubes 4 picked up from the secondary lane 31 fill alternate locations of a same row along container 9.

In the embodiment shown, the multiple pick up device 60 is provided with ten single pick up devices 600 (FIG. 8-FIG. 9); therefore, in two subsequent pick up operations, a row of twenty locations of test tubes is filled on container 9, which being typically square in shape, can therefore contain 20×20=400 of them. The discussion does not change if the numbers are different.

Figure 10:
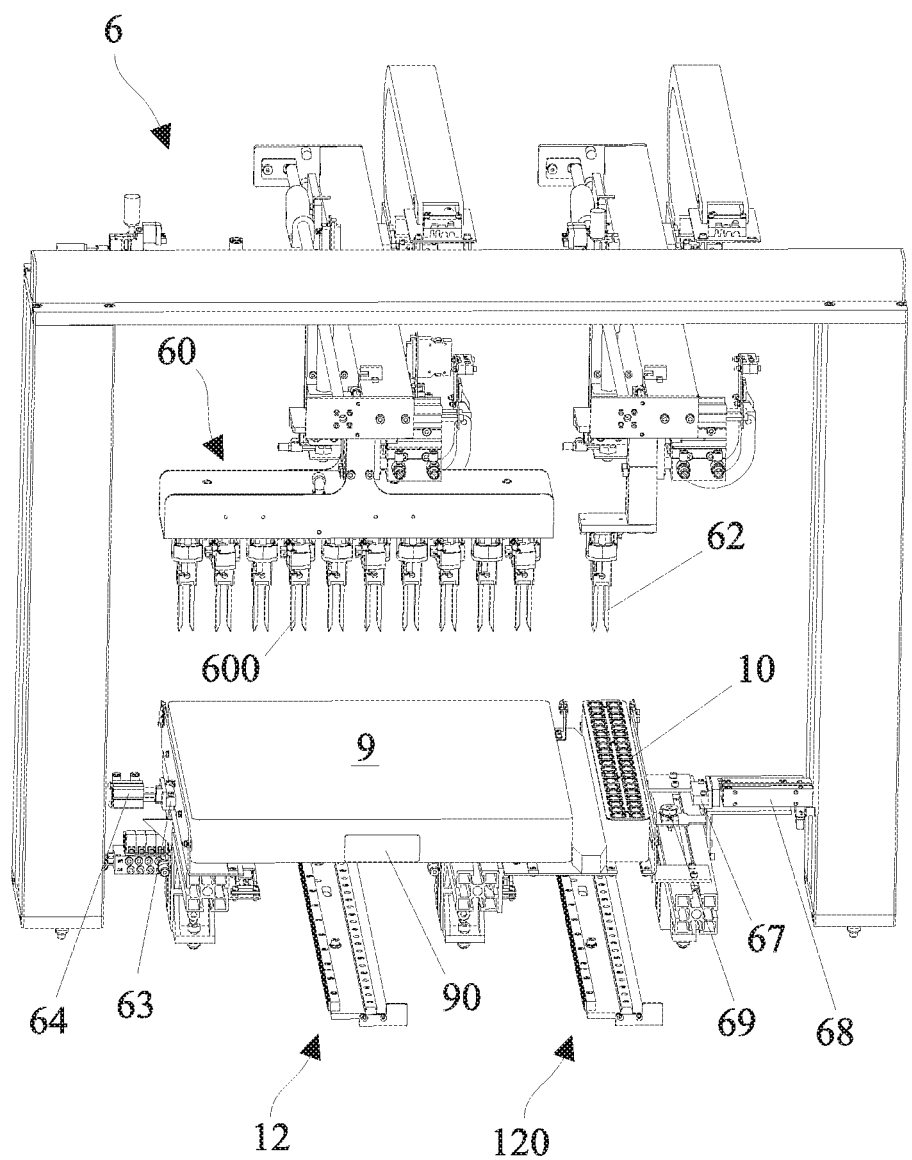
FIG. 10 shows a front perspective view of the sample input/output module.

Through the repetition of this cycle, the entire container 9 is preferably but not necessarily filled; during this operation, container 9 is locked in position by a rubber buffer 63 acting laterally in relation to container 9, and is pushed by a pneumatic cylinder 64 (FIG. 10). At the same time, an antenna 65, also placed in position by means of a pneumatic cylinder 66 (FIG. 11), reads an identifier (such as a barcode) of container 9, typically located at the bottom of the lower base of the same, for tracking the position thereof along apparatus 1.

Figure 11:
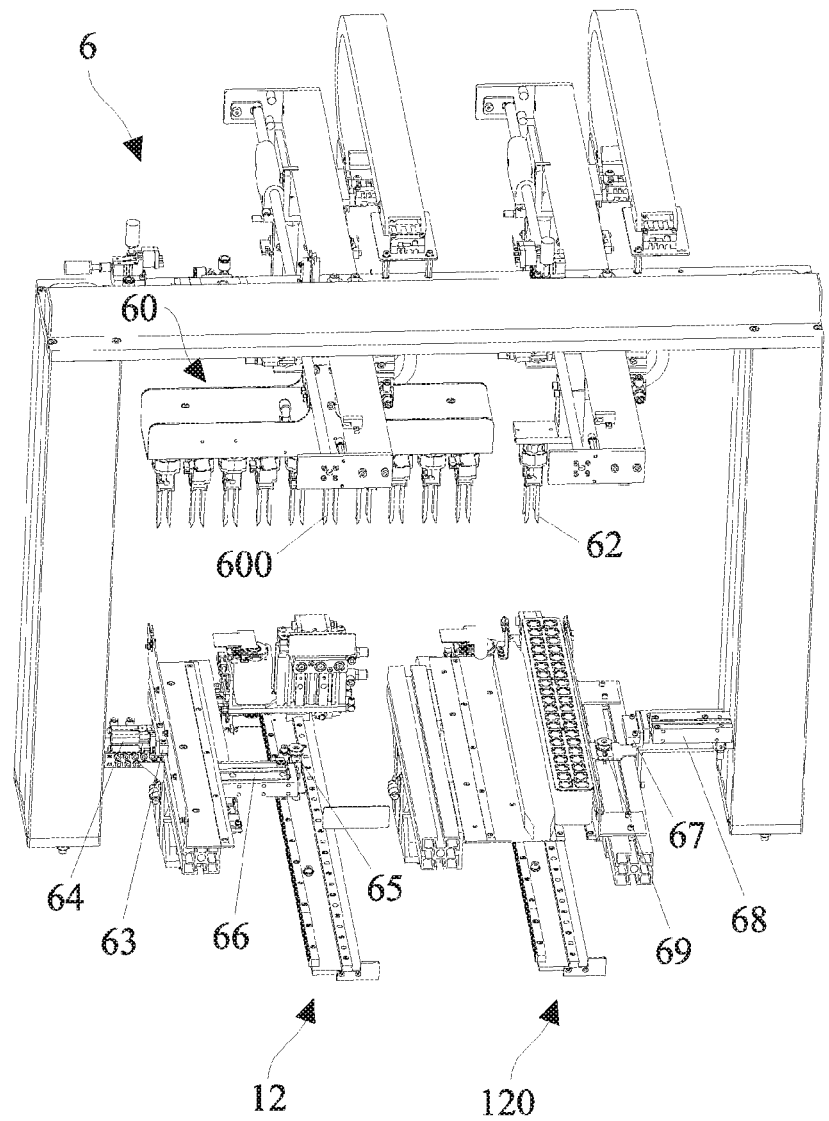
FIG. 11 shows a view similar to the previous one, having removed the test tube container.

The input/output module 6 likewise has similar locking devices for container 10, which shall be discussed in more detail hereafter, i.e. a rubber buffer 67 pushed by a cylinder 68 and an antenna 69 for identifying container 10 itself (FIG. 10-FIG. 11).

Figure 12:
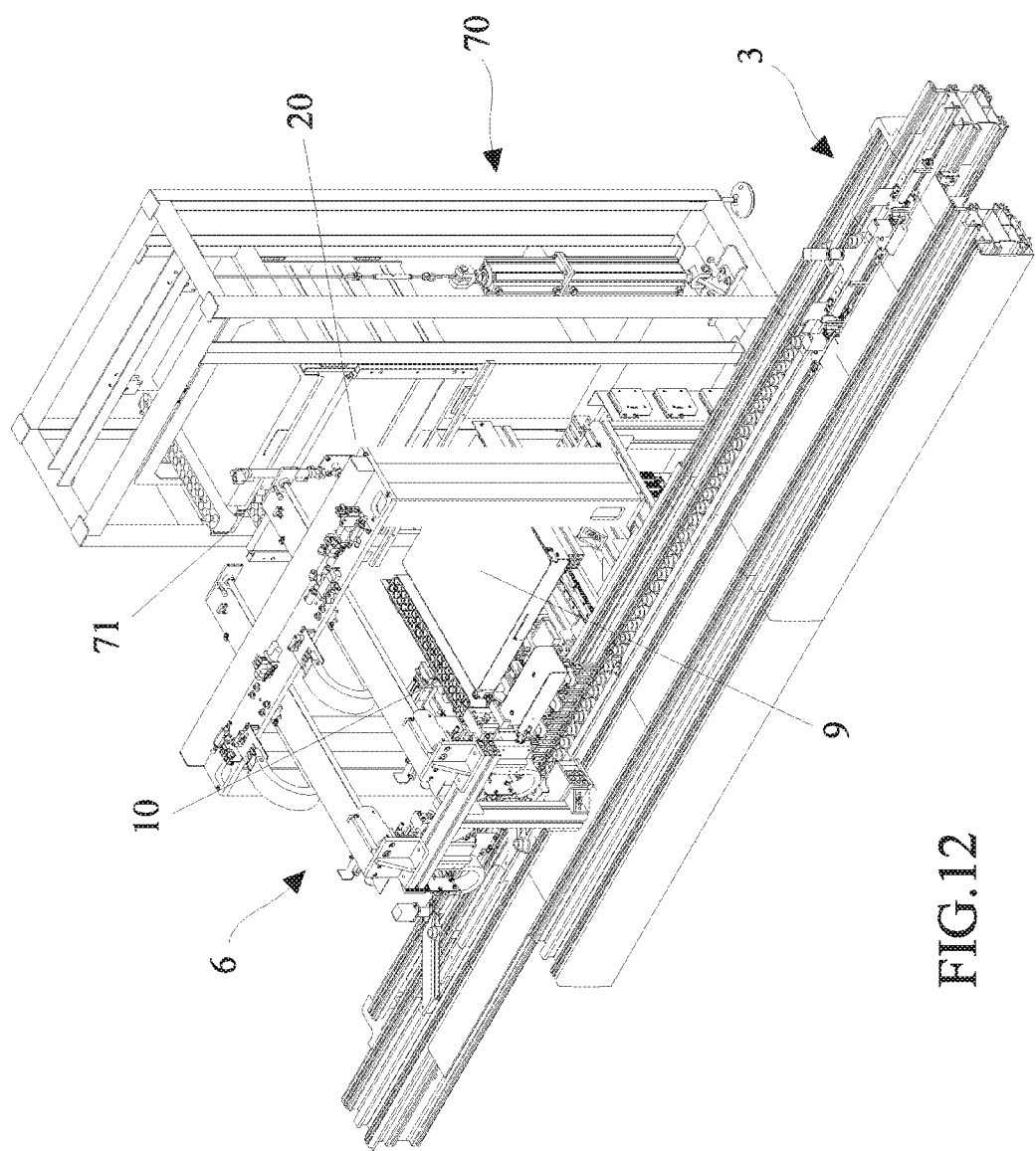
FIG. 12 shows a perspective view of the insertion step of a container into the warehouse.

Container 9, once full, must then be directed to warehouse 2: therefore, a sliding door 20 is raised and container 9 is made to slide on a first station 70 for the provisional allocation of containers 9, 10 provided with a certain number (in this example, four) of different shelves 71, each consisting of a space for accommodating a container 9 and a narrower container 10 (FIG. 12). This is in order to provisionally "park" up to four containers 9 and four containers 10 therein, managing the exchange of samples in the two directions (from system 3 to warehouse 2 and vice versa) and considering the absolute necessity, during the steady operation of apparatus 1, to parallelize the operations as much as possible.

Figure 13A:
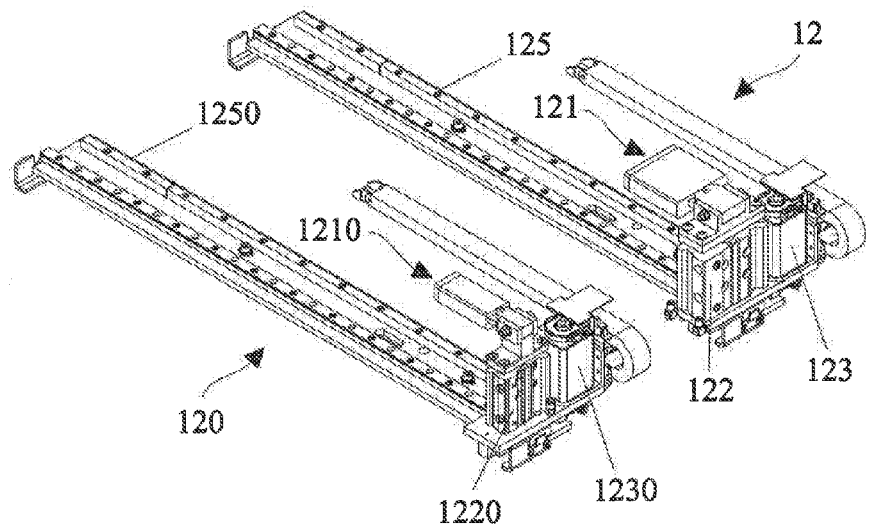
FIG. 13 consists of FIGS. 13A and 13B showing two perspective views, rotated by 180° relative to each other, of sliding mechanisms of the test tube containers, used in the input/output module.
Figure 13B:
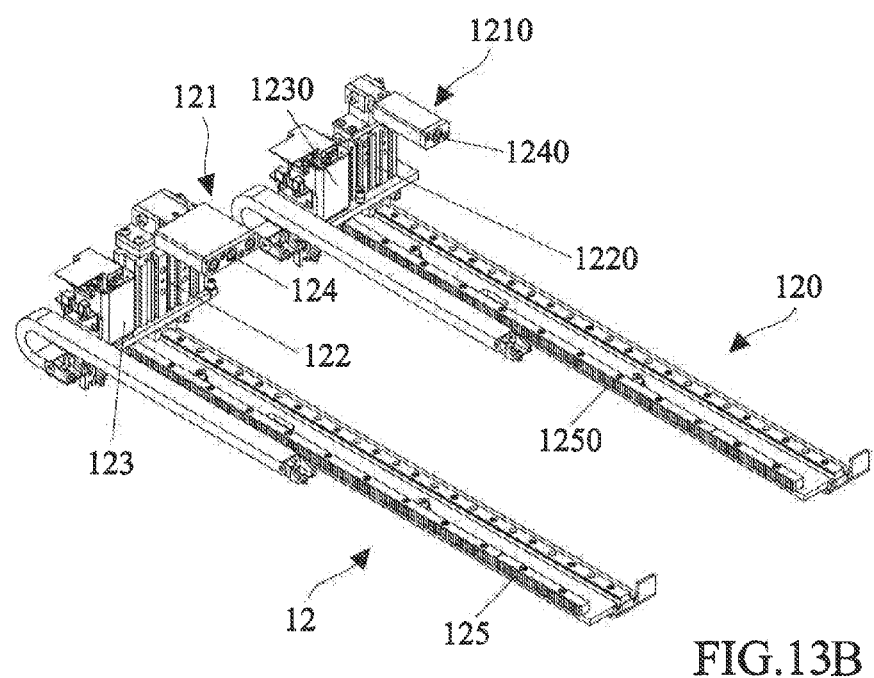

As regards container 9, the sliding takes place by means of a sliding mechanism 12 directly present on board of the input/output module 6, which also seats a similar sliding mechanism 120 dedicated instead to the sliding of a container 10 (FIG. 13A-FIG. 13B). Both sliding mechanisms 12 and 120 work in both sliding directions, pushing containers 9, 10 from the input/output module 6 to the first station 70 for the provisional allocation or vice versa, dragging them to carry out the opposite movement.

The sliding mechanism 12 is provided with a pusher 121 (FIG. 13A-FIG. 13B) which is able to rise from a resting position, thanks to a pneumatic cylinder 122, and to advance thanks to the action of a motor 123 along a rack 125, simultaneously catching container 9 thanks to the presence of magnets 124 on the wall thereof which are coupled, in the lifting step controlled by cylinder 122, with a magnetic strip 90 which is provided on the lateral surface of container 9 (FIG. 4). The action of motor 123 (FIG. 13A-FIG. 13B) drags container 9 in the direction orthogonal to the automation system 3, i.e. of insertion in the first station 70 for the provisional allocation.

The sliding mechanism 120 (FIG. 13A-FIG. 13B) has similar components which perform the same tasks, i.e. a pusher 1210, a pneumatic cylinder 1220, a motor 1230 and a rack 1250 along which pusher 1210 advances, which has a magnet 1240 adapted to mate with a magnetic strip 900 of container 10 (FIG. 4) and drag it in the direction orthogonal to the automation system 3.

At the first station 70 for the provisional allocation (FIG. 15), shelves 71 move vertically taking four different positions to present each time, depending on the specific needs, one of the four shelves 71 to the interface with the input/output module 6 on one hand and with the traveling lift 8 on the other, and thus to carry out the suitable translations of containers 9 and/or 10.

Figure 15:
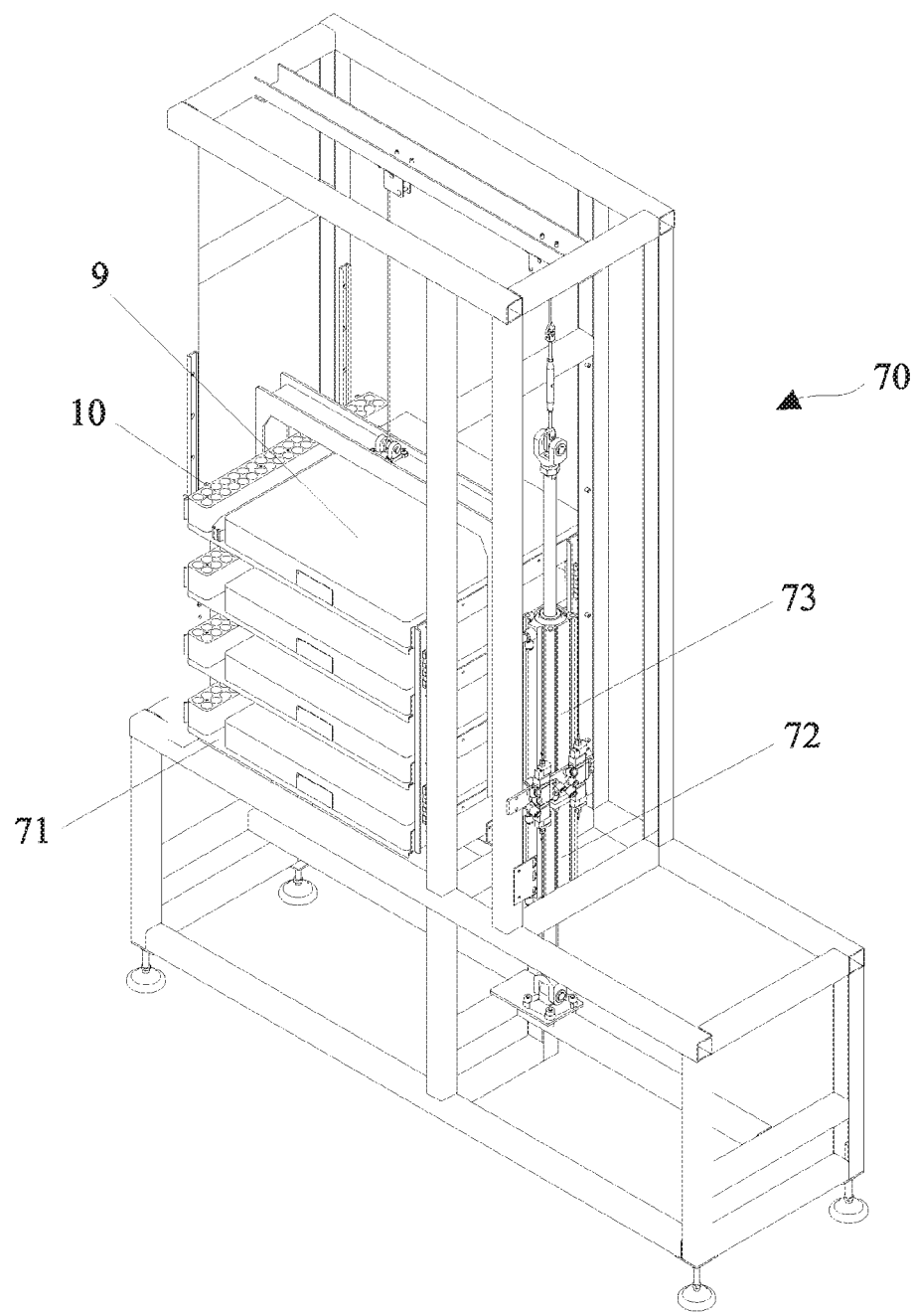
FIG. 15 shows a perspective view of a first station for the provisional allocation of containers.

The vertical movement of shelves 71 of the first station 70 is carried out thanks to two pneumatic cylinders 72 and 73 aligned in height. The two cylinders have a different height, and being both able to take both a high and a low position, the four possible combinations that can be achieved ("low-low"; "low-high"; "high-low"; "high-high") give rise to the four different heights of the first station 70 (FIG. 15).

Figure 14A:
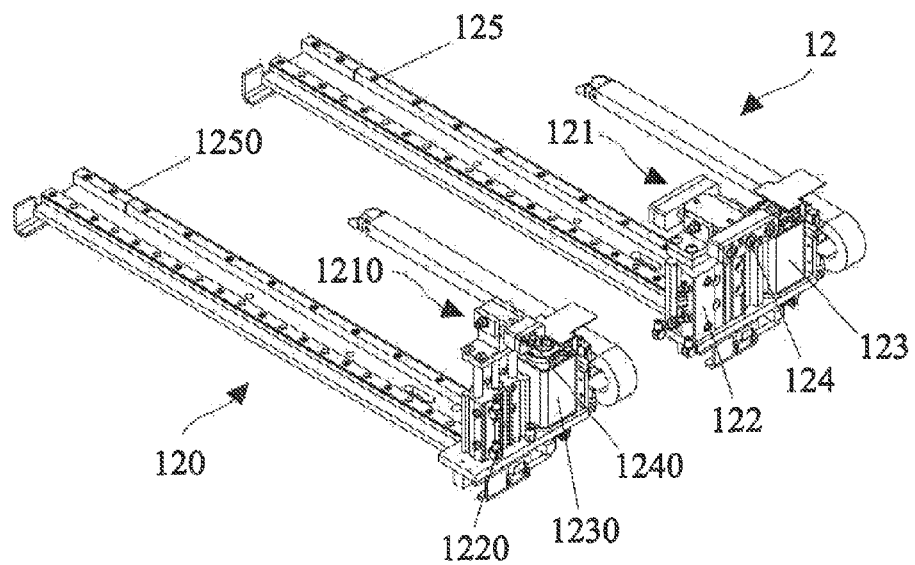
FIG. 14 consists of FIGS. 14A and 14B showing two perspective views, rotated by 180° between them, of sliding mechanisms of the test tube containers, used in the traveling lift.
Figure 14B:
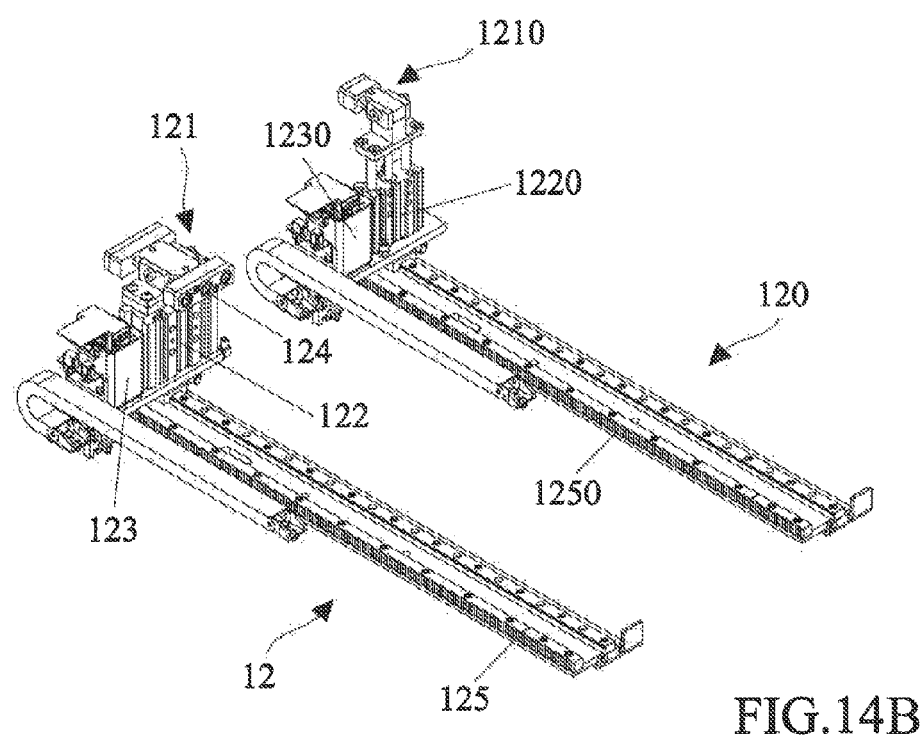

Returning to the path of container 9 full of test tubes 4 just picked up from system 3, it therefore is on the first station 70 for the provisional allocation, facing the traveling lift 8 which then picks it up thanks to a sliding mechanism 12 that it accommodates on board (FIG. 14a-FIG. 14b), similar to that already described above with reference to the input/output module 6, though with a small difference that shall be better described hereafter. The magnetic system of sliding mechanism 12 in this case drags container 9, from the first station 70 to the traveling lift 8, rather than a push as described above for the passage of container 9 from the input/output module 6 to the first station 70. The traveling lift 8 is also provided with a sliding mechanism 120 for container 10, which is also similar to that already shown in the input/output module 6 (FIG. 14A-FIG. 14B).

Figure 17:
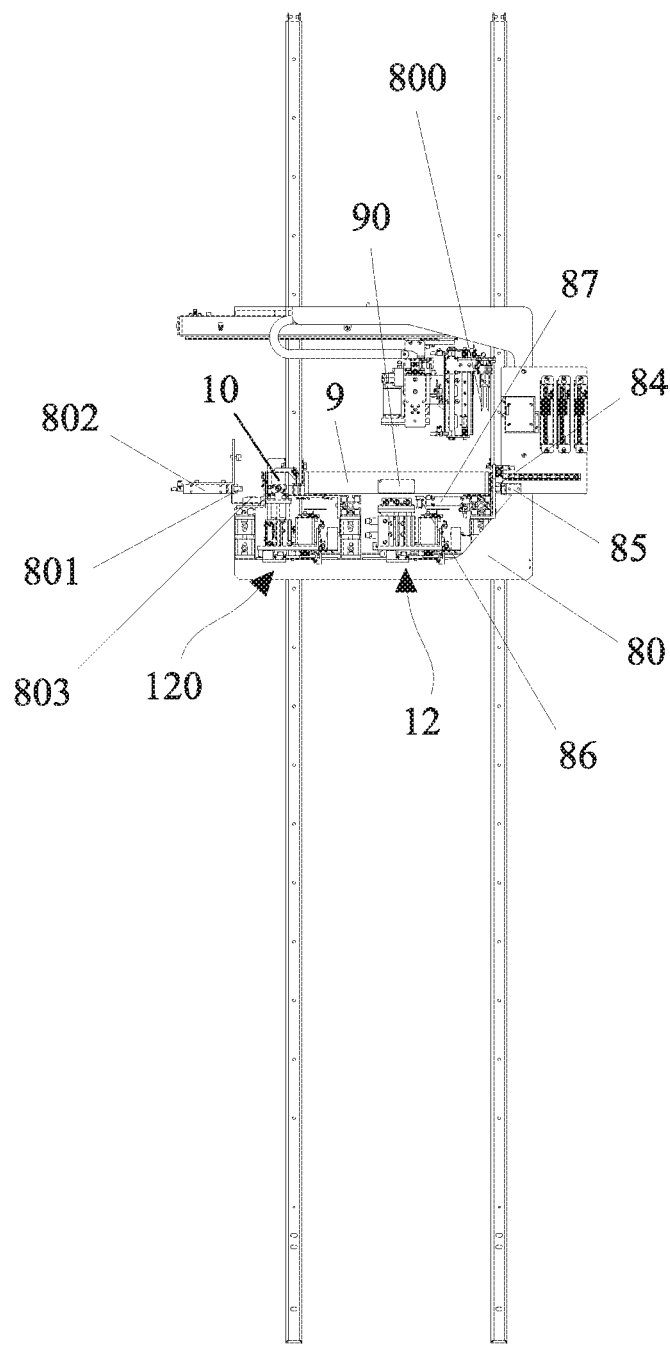

On the traveling lift 8 there are also a locking mechanism of container 9 on a shelf 80 intended to receive it, comprising a rubber buffer 84 pushed by a pneumatic cylinder 85, and a mechanism for detecting the identifier of container 9 through an antenna 86 with pneumatic cylinder 87 (FIG. 17).

Figure 18:
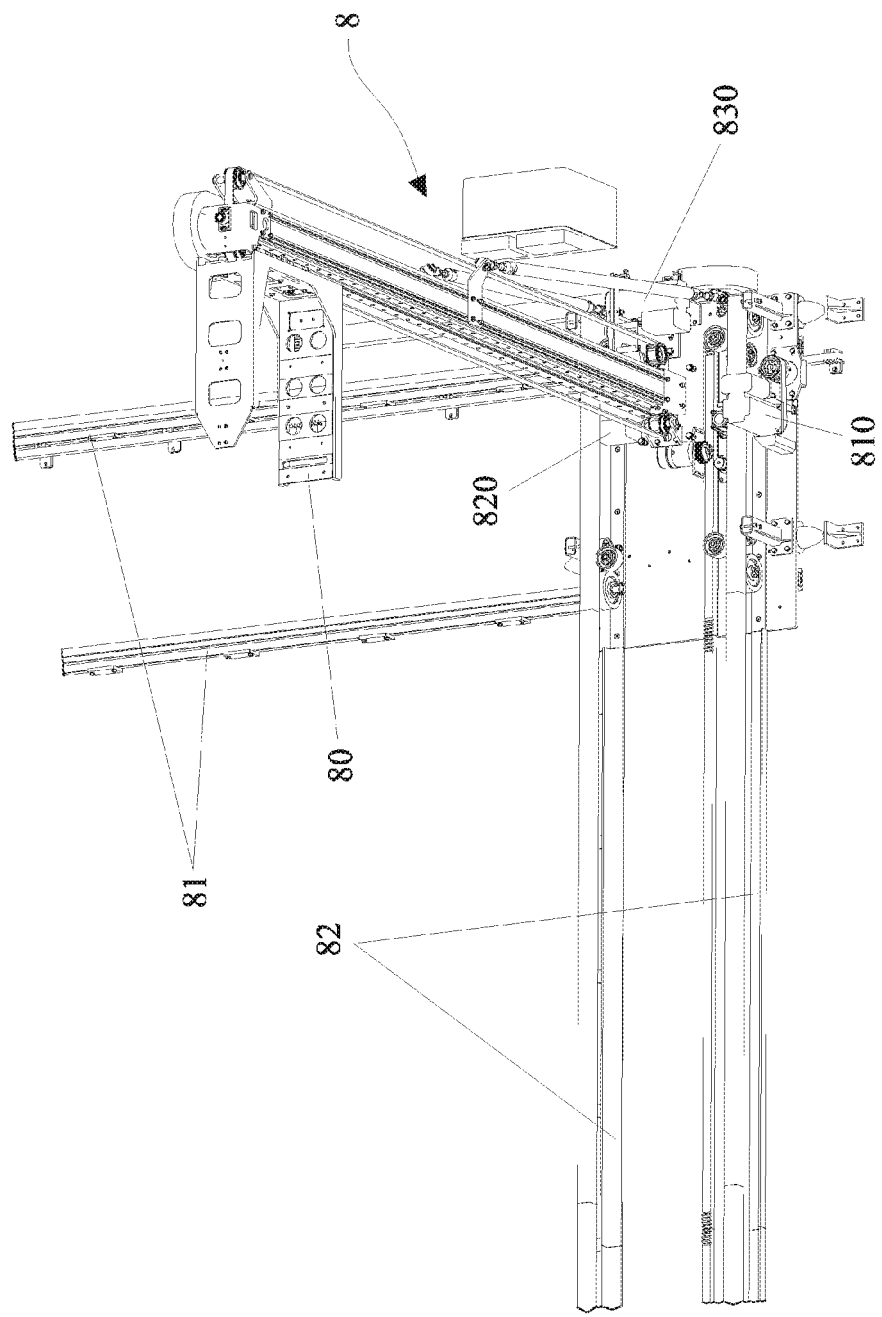
FIG. 18 shows a rotated top view of the traveling lift.

At this point, the traveling lift 8 is designed to move container 9 which it has on board towards the appropriate shelf inside warehouse 2. To do so, the traveling lift 8 moves first along a first pair of rails 81 thanks to the action of a first motor 810, to position itself at a specific lane in which then it penetrates, being driven by a second motor 820, along a second pair of rails 82 present at each lane (FIG. 18, which shows only one of such pairs of rails 82); this allows the traveling lift 8 to reach the correct column of the predetermined shelf.

Figure 19:
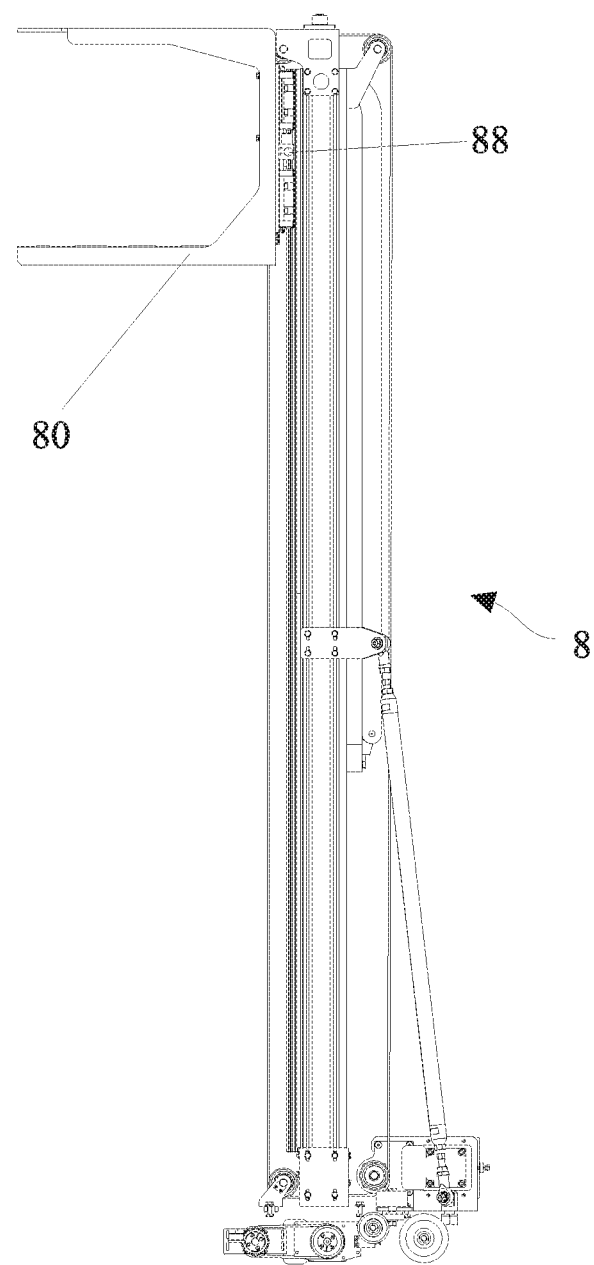
FIG. 19 shows a lateral view of the traveling lift.

Afterwards, in order to complete the positioning operation, shelf 80 of the traveling lift 8, where container 9 is accommodated, is lifted by means of a third motor 830 (FIG. 18) until it arrives exactly in front of the free location 11 of the shelf. Maintaining the correct height along the vertical is ensured by a latch 88 (FIG. 19), which suitably locks shelf 80 at the desired height, also carrying out a safety function to prevent a sudden failure of the traveling lift 8 (for example, due to power failure) from causing the collapse of shelf 80 itself.

The insertion of container 9 into location 11 can proceed only if a correct alignment is ensured between the traveling lift 8 (and in particular shelf 80 thereof, which carries container 9) and location 11 which must receive container 9.

Such an alignment is basically already achieved in the first instance, but nevertheless it requires a "fine-tuning" system before proceeding to the actual translation of container 9. This final adjustment, which has extreme precision requirements, can be carried out by providing the traveling lift 8 with a reader 83 which frames an identifier 111 (typically a two-dimensional barcode or "data matrix") positioned on the side of each of locations 11 of each shelf and which therefore uniquely defines location 11 itself inside warehouse 2 (FIG. 16).

The adjustment system, detecting the deviation of the traveling lift 8 with respect to a known position and referred to a perfect centering according to this framing, is able to command slight deviations in the two directions to motors 820 and 830 (FIG. 18) until reaching the expected optimal position.

Since upon the penetration of the traveling lift 8 inside one of the lanes of warehouse 2 it is located between two shelves facing each other, in both of which it can insert or withdraw containers 9, it is possible to have a second adjustment system, and therefore a second reader 83 (FIG. 16), which frames identifiers 111 positioned on the mirror shelf along the same lane.

Figure 16:
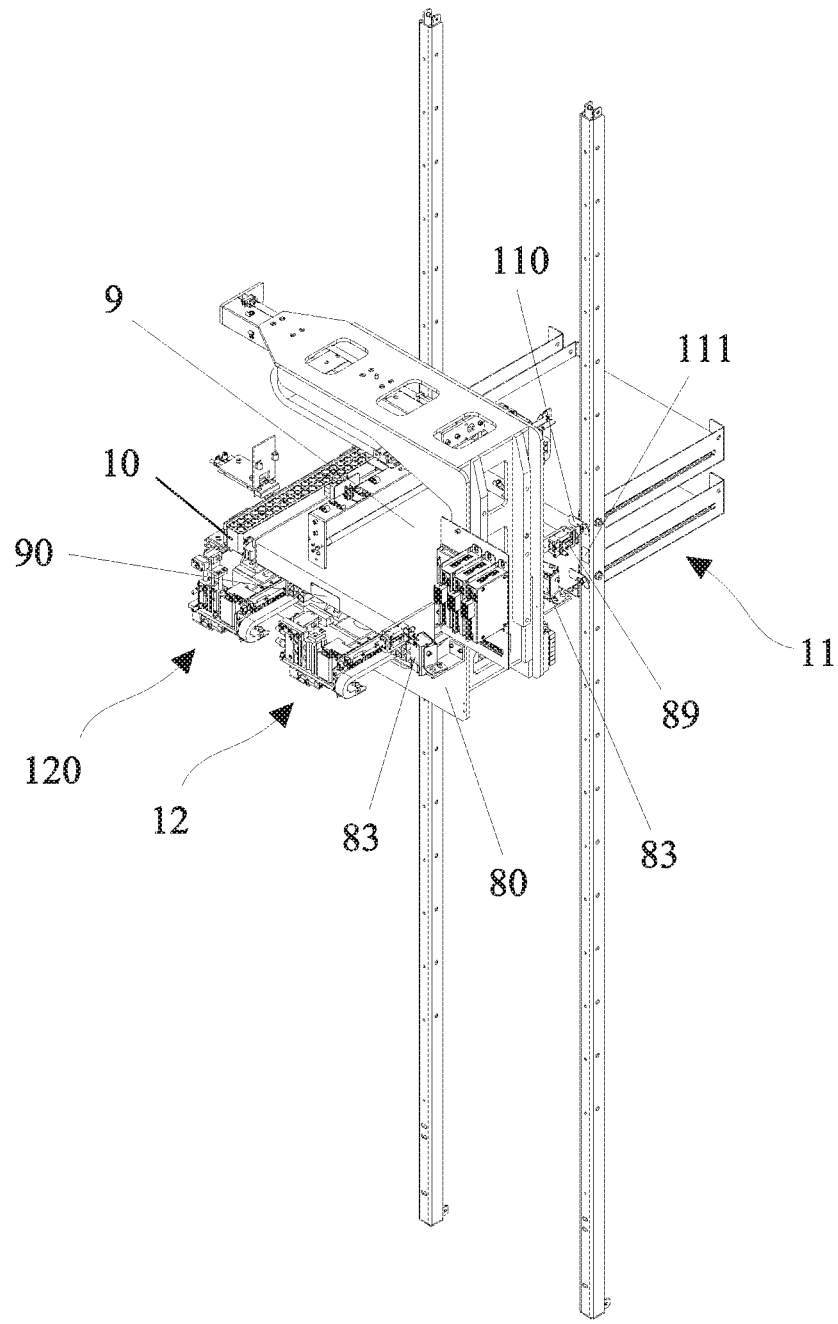
FIG. 16 and FIG. 17 show a perspective and a front view, respectively, of the test tube containers on board of the traveling lift.

Once the perfect positioning of the traveling lift 8 is ensured, the sliding mechanism 12 on board of the traveling lift 8 inserts the full container 9 into location 11; in order to do so, a pneumatic cylinder 89 is also involved, also located on hoard of the traveling lift 8, which lifts a safety latch 110 located on the side of each location 11 and which would normally prevent the insertion of a container 9 into location 11 (FIG. 16). Of course, once container 9 has been inserted into the appropriate location 11, the pneumatic cylinder 89 releases the safety latch 110 that thus suitably locks on the input/output side container 9, then closed on the other side by the wall of the shelf.

This ensures the retention of container 9 into location 11, even in case of stresses (such as seismic) to which warehouse 2 may be subject.

The sliding mechanism 12 on board of the traveling lift 8 (FIG. 14A-FIG. 14B) is designed to drag in both directions a container 9 hosted thereby, and insert it when required in a specific location 11 of a shelf or in the respective location 11 of the mirror shelf thereof.

In order to make this possible, pusher 121 of the sliding mechanism 12, when in "low" position, can slide along rack 125 substantially passing underneath container 9 hosted by shelf 80, to then hook container 9 itself, after having moved to the "high" position thanks to the pneumatic cylinder 122, and drag in the opposite direction. In fact, the sliding mechanism 12 of the traveling lift 8 is slightly modified by the presence of magnets 124 on both sides of pusher 121 (FIG. 14A-FIG. 14B) in order to push in both directions container 9, thanks to the fact that each container 9 used is provided with a magnetic strip 90 on the other lateral surface thereof as well.

The difference with the sliding mechanism 12 described above with reference to the input/output module 6 (FIG. 13A-FIG. 13B), in which the sliding of container 9 takes place in both directions but alternatively by means of a push or dragging by pusher 121 with magnets 124, which hook container 9 always from the same side, is therefore clear.

On the other hand, there are no substantial differences between the sliding mechanism 120 used in the traveling lift 8 (FIG. 14A-FIG. 14B) and that used in the input/output module 6 (FIG. 13A-FIG. 13B). In fact, magnet 1240 is also here on a single side of pusher 1210, because unlike container 9, container 10 must not enter into the shelves of warehouse 2 and thus there is no need to push it alternately in the two opposite directions.

The traveling lift 8, after unloading a container 9 into the appropriate location 11 of warehouse 2, may provide for the retrieval of some test tubes 4 already stored in the other shelves of warehouse 2, because for example some analysis must be carried out of such samples. Optionally, it can also provide to the retrieval of a new empty container 9 (if available) to be then positioned on the input/output module 6.

The need to proceed immediately with such operations depends on the specific requirements, but the trend must be of course to optimize as much as possible the operation flow of the traveling lift 8, before it returns towards the input/output module 6 and thus towards the automation system 3.

For the retrieval of the test tubes 4, the traveling lift 8 (which in the meantime has suitably moved in front of a location 11 of a specific shelf, also thanks to the adjustment system described above) releases the safety latch 110 of the location 11 concerned (FIG. 16) by means of the pneumatic cylinder 89, so that the full container 9 contained therein can be pulled by the sliding mechanism 12 of the traveling lift on its shelf 80.

At this point, a single pick up device 800 of test tubes, i.e. a Cartesian robot, present on the traveling lift 8 selectively picks up one or more test tubes 4 from container 9 to move them into container 10 for the test tubes to be retrieved, locked into position by a rubber buffer 801 pushed by cylinder 802, integral with an antenna 803 for the recognition of the identifier (barcode) of container 10 (FIG. 17).

It is noted that container 10 is on the traveling lift 8, typically because it has previously translated as well (via the sliding mechanisms 120) from the input/output module 6 to the first station 70 of the provisional allocation and from this to the traveling lift 8.

Once the selective retrieval of test tubes 4 from container 9 has ended, it is inserted back into its location 11 and the pick up can certainly continue on other test tubes 4 of another container 9 in another location 11 of warehouse 2, in front of which the traveling lift 8 moves in the meantime, always with the partially filled container 10 on board. The cycle is typically (but not necessarily) repeated up to the total filling of container 10.

Finally, the traveling lift 8 as said can also load a new empty container 9, to be then directed to the input/output module 6 so that it can accommodate new test tubes 4 therein from the automation system 3.

The traveling lift 8 with the empty container 9 and the full container 10 on board now returns to the automation system 3, and in particular it unloads both the empty container 9 and the full container 10 on the first station 70 for the provisional allocation, which then makes available the two containers 9, 10 to the input/output module 6, depending on its filling conditions at steady state; all is carried out by suitably coordinating the vertical movements of shelves 71 of the first station 70 (FIG. 15) with those of the two pairs of sliding mechanisms 12 and 120, i.e. both the pair on board of the traveling lift 8 (FIG. 14A-FIG. 14B) and that on board of the input/output module 6 (FIG. 13A-FIG. 13B).

Once container 10 has reached the input/output module 6 and has been suitably locked by the buffer rubber 67, pushed by cylinder 68 and identified by antenna 69 (in FIG. 10-FIG. 11 for convenience of illustration these components are shown not still in action, i.e., on the side of container 10), the test tubes 4 contained therein are picked up by a single pick up device 62 (FIG. 7-FIG. 11) which positions them along a further secondary lane 32 (FIG. 6) of the automation system 3, along which empty transport devices 5 have been previously diverted, used just to accommodate the test tubes 4 just retrieved from inside warehouse 2.

The pick up device 62 has two different pick up positions on container 10 as well, in order to draw test tubes 4 in both locations on the same row. The movement of the pick up device 62 is therefore also controlled by a pneumatic cylinder 620 (FIG. 9) able to move the pick up device 62 between the two positions, at the interface with container 10, while the next unloading position of the test tube 4 picked up in the transport device 5 waiting along the secondary lane is unique.

Each of the test tubes 5 concerned, once returned on the automation system 3, is typically identified (for example by means of a barcode reader combined with a device for rotating the transport device 5) so as to create the proper association with the transport device 5 that has just received it, and then directed along other modules for possible new analysis.

Apparatus 1 also includes, as mentioned, the discharge of test tubes 4 that, having exhausted their lifetime, have no reason anymore to be stored into warehouse 2.

The disposal relates to one container 9 at a time, regardless of whether it is, as preferable, completely full of test tubes 4 or partially empty.

The storage time in warehouse 2 after which there is the need to dispose of a given container 9, and therefore of all the test tubes 4 which it contains, is configurable and is typically in the order of a few days.

It is again the traveling lift 8 that picks up container 9 to be disposed of, and to direct it towards the area of warehouse 2 opposite to that which interfaces with the automation system 3, where the discharge device 13 of test tubes 4 is positioned (FIG. 5).

Figure 20:
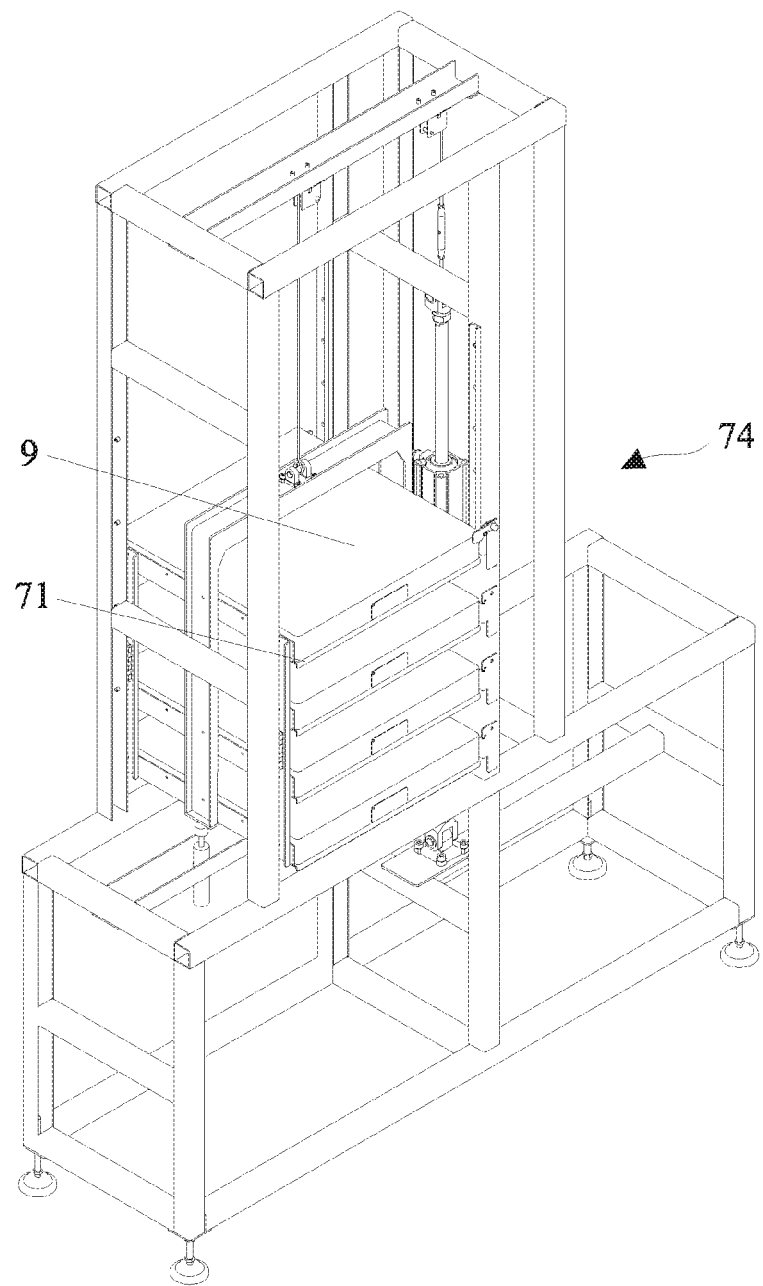
FIG. 20 shows a perspective view of a second station for the provisional allocation of containers.

The directing of containers 9 with test tubes 4 to be disposed of to the discharge device 13 uses a second station 74 for the provisional allocation (FIG. 20) similar to that present at the interface with the input/output module 6, except for not having an area dedicated to containers 10, which are not involved in the disposal.

Figure 21:
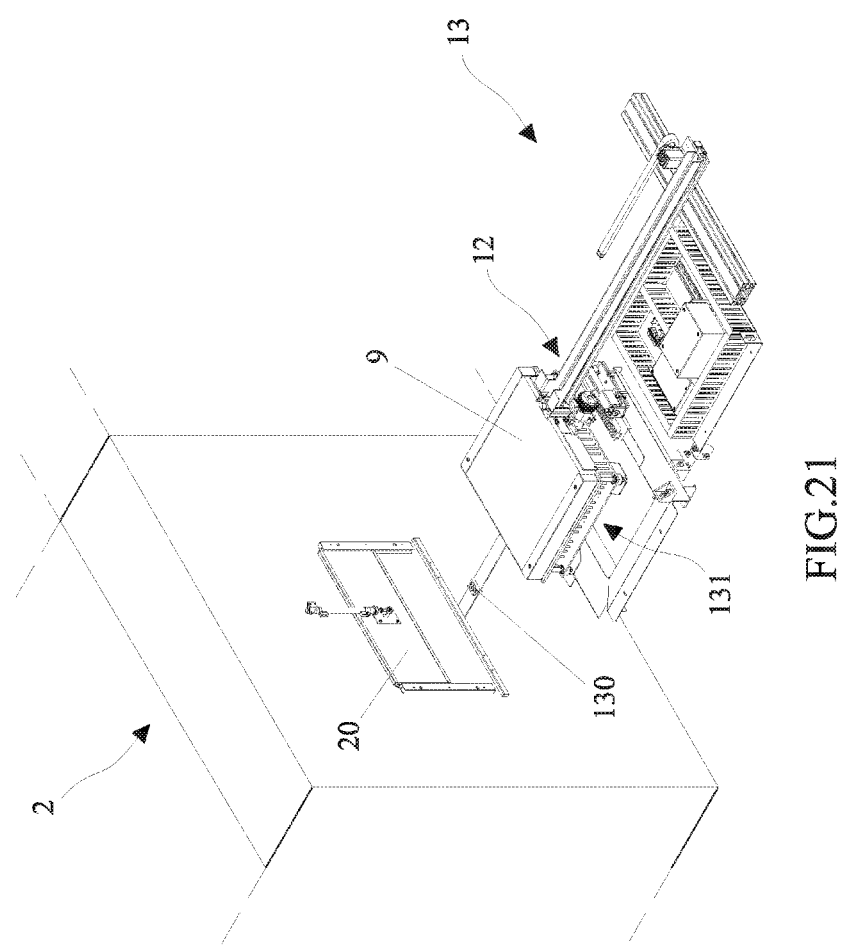
FIG. 21 shows a perspective view of some details of the discharge device.

Container 9 picked up by the traveling lift 8 is suitably dragged by the sliding mechanism 12 of the traveling lift 8 itself on the second station 74 for the provisional allocation, and hence subsequently picked up, through a sliding door 20, by a sliding mechanism 12 similar to those already seen but located on board of the discharge device 13 (FIG. 21).

During this operation, container 9 is locked for a few moments to be as usual identified by an antenna 130.

Figure 22:
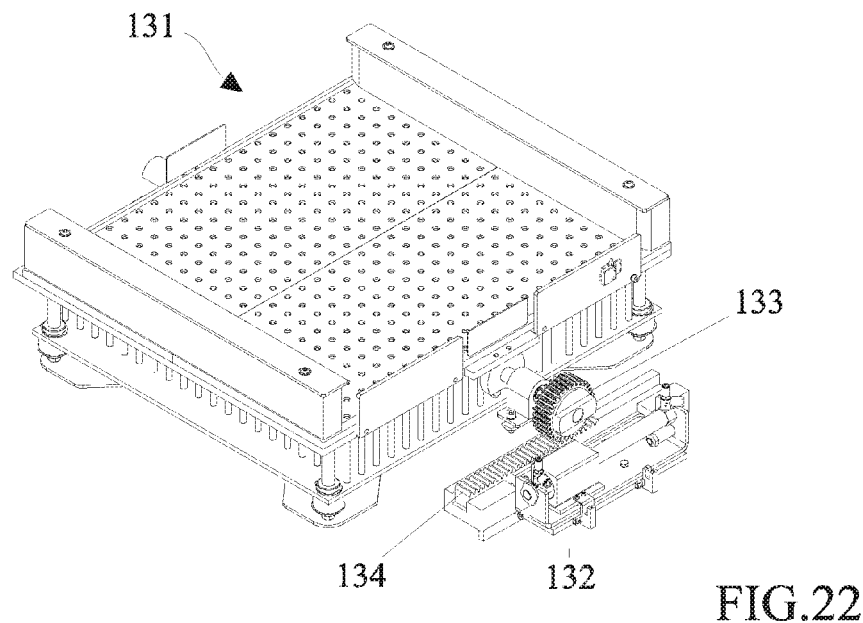
FIG. 22 and FIG. 23 show two perspective views, overturned by 180° relative to each other, of a discharge position of a container in the discharge device, having removed the container itself.

Once arrived into the appropriate discharge position 131, container 9 is turned upside down thanks to a pneumatic cylinder 132 which, by actuating a gear comprising a pinion 133 and a rack 134, causes the overturning of the surface on which container 9 is resting (FIG. 22, where container 9 has been removed).

The test tubes 4 therefore end up in a position below, where as said there may be an apparatus with multiple racks 14 (FIG. 5), or in any case a collection point of the test tubes 4 to be disposed of with any other configuration (for example, a single collection tank of the same or a belt which then drags them elsewhere; the configuration may depend on the space actually available in the laboratory).

Figure 23:
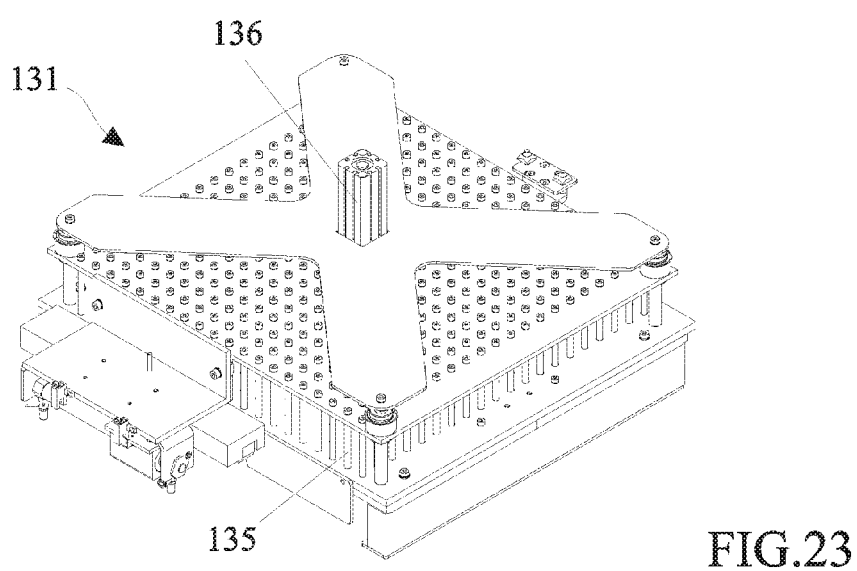

The discharge device 13 may comprise a pushing mechanism for each test tube 4 in each of the seats of container 9, comprising plugs 135 actuated by a pneumatic cylinder 136 which act after the overturning of container 9 so as to ensure with certainty the simultaneous expulsion of all the test tubes 4 from the respective seats (FIG. 23).

Container 9, once emptied, is overturned again to be returned to the initial position; then, plugs 135 are retracted and then the sliding mechanism 12 returns container 9 first on the second station 74 for the provisional allocation, then on the traveling lift 8 and finally in one of the shelves of warehouse 2.

Apparatus 1 may be provided with a spare input/output module 6000 (FIG. 1 and FIG. 6), which remains parked adjacent to the automation system 3 to come into play only when necessary, i.e. in case of breakage of the "main" input/output module 6.

The same applies to the insertion into warehouse 2 of an equally spare traveling lift 8000 (FIG. 3), to be used only if the "main" traveling lift 8 breaks down or needs routine maintenance.

If in fact the traveling lift 8 breaks down, for its maintenance it is preferable to move it outside warehouse 2, for a twofold safety requirement of maintainers, who are thus not forced to work inside warehouse 2, possibly at low temperatures, also preventing the risk of interfering with the movement of the traveling lift 8000 which meanwhile has been activated. To extract the traveling lift 8, when broken, from warehouse 2, the latter is provided with a door 200 (FIG. 1) obviously high at least as the traveling lift 8, through which it is dragged out sliding along the second pair of rails 82. Once this sliding has been completed, door 200 closes back, so that the isolation of the environment inside warehouse 2 is again ensured and as a result the entire apparatus 1 can be put back into operation; at the same time, the traveling lift 8 can be safely repaired, in the outside, by one or more maintainers.

The innovative aspect of the invention is therefore represented by the substantial increase, compared to known apparatus that use a traveling lift 8 for the storage of objects and in particular of containers 9 of test tubes 4, in the throughput of storage/retrieval of samples; this is undoubtedly thanks to the simultaneous loading of multiple test tubes 4 at a time (ten, in the embodiment shown) from an automation system 3 to an input/output module 6 and vice versa, but also thanks to the particular configuration of the traveling lift 8, which simultaneously accommodates containers 9 of test tubes to be stored and containers 10 of test tubes to be retrieved, and suitably parallelizes the storage/retrieval operations according to the variable needs of the moment.

The increased throughput makes it possible indirectly to build a larger warehouse 2 in terms of number of containers 9 of test tubes that it can accommodate.

Moreover, as regards in particular the retrieval of samples to re-enter along the automation system 3, particularly innovative is the possibility, where appropriate, to can out such a retrieval not on the entire quantity of test tubes 4 stored in a same container 9, but possibly also on single test tubes 4 belonging to different containers 9 and then directed towards the automation system 3 using container 10 of test tubes to be retrieved.

Moreover, thanks to the safety latch 110 which locks each container 9 inserted into locations 11 of warehouse 2, each of such containers 9 remains locked inside the shelf, on the other side there being the wall of warehouse 2 itself; the lock is ensured even in case of earthquake.

Several changes and variations may be made to the invention thus conceived, all felling within the scope of the inventive concept.

In the practice, the materials used as well as shapes and sizes, may be any, according to the requirements.

The invention claimed is:

1. An apparatus for storage and retrieval of large volumes of test tubes in/from a warehouse, wherein it comprises
    an input/output module of test tubes from/to an automation system for the transport of said test tubes in transport devices of single test tubes, which includes two distinct coplanar locations for a first and a second container of a plurality of test tubes,
    a multiple pick up device adapted to pick up said test tubes from a plurality of transport devices of single test tubes queued in a secondary lane of said automation system, and to release them in the first container positioned on an input/output module,
    a single pick up device adapted to pick up said test tubes from the second container positioned on said input/output module and to release them in said transport devices of single test tubes on said automation system,
    a first station for the provisional allocation of said containers on distinct locations of a same shelf comprising one or more shelves and interfaced with said input/output module,
    a second station for the provisional allocation of the first container on one or more shelves, interfaced with a discharge device of test tubes to be disposed,
    a motorized traveling lift able to simultaneously transport on two distinct coplanar locations said first and second container, and adapted to bidirectionally move said first and second container of test tubes between said first station for the provisional allocation and said warehouse, and only said first container between said warehouse and said second station for the provisional allocation.

2. The apparatus according to claim 1, wherein said traveling lift comprises:
    a sliding mechanism adapted to drive in both directions a first container hosted in it, and when necessary insert it in a given location of a shelf of the warehouse,
    a single pick up device for a selective retrieval of one or more test tubes contained in a first container dragged out from one location of said warehouse by means of said sliding mechanism, said retrieved test tubes being inserted in a second container stationary on the traveling lift,
    means for adjusting the positioning of the traveling lift comprising one or more readers adapted to frame an identifier positioned in the vicinity of each of said locations of said warehouse for detecting the deviation of said traveling lift with respect to a position of perfect centering, the actuation of motors of said traveling lift allowing the achievement of said perfect centering,
    locking and identification means of said first and second container.

3. The apparatus according to claim 1, wherein in said multiple pick up device, the distance between each of the single pick up devices is appropriately calibrated on the distance between the test tubes of two adjacent transport devices of single test tubes queued in said secondary lane of the automation system, said distance being twice the distance between two adjacent locations of the first container which provides for each row a double number of locations with respect to the number of pick up devices, said multiple pick up device being able to perform a further movement, controlled by a pneumatic cylinder and of width equal to half the pitch between two pick up fingers, so that two successive series of test tubes picked up from the secondary lane fill alternate locations of a same row along the first container.

4. The apparatus according to claim 3, wherein said single pick up device includes a pneumatic cylinder able to move the pick up device between two different pick up positions on the second container in order to pick test tubes in both locations in the same row, while the successive discharge location of the test tube picked up in the transport device of single test tubes waiting on further secondary lane of the automation system is unique.

5. The apparatus according to claim 1, wherein said stations for the provisional allocation are provided with pneumatic cylinders aligned in height in a number equal to half of the shelves provided so as to make these take various position combinations.

6. The apparatus according to claim 1, wherein said input/output module comprises:

a first sliding mechanism for said first container, which includes a pusher which is able to rise from a resting position, thanks to a pneumatic cylinder, and to advance thanks to the action of a motor along a rack, simultaneously catching the first container thanks to the presence of magnets on a wall thereof which are coupled, in the lifting step controlled by the cylinder, with a magnetic strip which is provided on the lateral surface of the container, the action of the motor dragging the first container in the direction orthogonal to the automation system, i.e. of insertion in the first station for the provisional allocation, a second sliding mechanism of said second container, which includes a pusher, a pneumatic cylinder, a motor and a rack along which the pusher advances, which has a magnet adapted to couple with a magnetic strip of said second container dragging it in the direction orthogonal to the automation system, i.e. of insertion in the first station for the provisional allocation.

7. The apparatus according to claim 6, wherein the sliding mechanism of the traveling lift is similar to said first sliding mechanism of the input/output module, but differs from the latter in that the pusher, when in "low" position, can slide along the rack passing under the first container to catch the first container itself, after having moved to the "high" position by means of the pneumatic cylinder, and drag it in the other direction, the sliding mechanism of the traveling lift having magnets on both sides of the pusher in order to push or pull in both directions the first container, thanks to the fact that each first container used is provided with a magnetic strip on the other lateral surface thereof as well.

8. The apparatus according to claim 1, wherein said discharge device includes an unloading position wherein the first container is turned upside down thanks to a pneumatic cylinder which, by actuating a gear comprising a pinion and a rack, causes the overturning of the surface on which the first container is resting, said discharge device comprising a pushing mechanism for each test tube in each of the seats of the first container, comprising plugs actuated by a pneumatic cylinder which act after the overturning of the first container so as to ensure with certainty the simultaneous expulsion of all the test tubes from the respective seats.

* * * * *